(12) United States Patent
Asp et al.

(10) Patent No.: US 6,337,185 B1
(45) Date of Patent: Jan. 8, 2002

(54) METHOD OF SEQUENCING

(75) Inventors: Allan Asp, Uppsala; Peder Carstenius, Enskede, both of (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/068,783

(22) PCT Filed: Nov. 13, 1996

(86) PCT No.: PCT/SE96/01464

§ 371 Date: Feb. 22, 1999

§ 102(e) Date: Feb. 22, 1999

(87) PCT Pub. No.: WO97/18328

PCT Pub. Date: May 22, 1997

(30) Foreign Application Priority Data

Nov. 16, 1995 (SE) ................................................ 9504099

(51) Int. Cl.$^7$ ........................... C12Q 1/68; C12P 19/34; C07H 21/04
(52) U.S. Cl. ........................ 435/6; 435/91.2; 435/91.5; 536/25.3; 536/25.32
(58) Field of Search .......................... 435/6, 91.2, 91.5; 536/24.3, 24.33, 25.3, 25.32; 422/50

(56) References Cited

FOREIGN PATENT DOCUMENTS

| EP | 0 371 437 A1 | | 6/1990 |
| EP | 371437 A2 | * | 6/1990 |
| WO | 92/10589 | * | 6/1992 |
| WO | WO 93 08305 | | 4/1993 |
| WO | 94/11529 | * | 5/1994 |

* cited by examiner

*Primary Examiner*—Carla J. Myers
*Assistant Examiner*—Diana Johannsen
(74) *Attorney, Agent, or Firm*—Royal N. Ronning, Jr.

(57) ABSTRACT

A method of analyzing a sequence of a polynucleotide of interest, comprising the steps of: a) incorporating one member of a specific binding pair at the end of each strand of a double stranded polynucleotide of interest, the number being of the same type for both strands, b) immobilizing both strands of the polynucleotide to a solid support provided with the other member of the specific binding pair, c) annealing sequencing primers to the immobilized strands, d) sequencing both strands by the chain termination method. The polynucleotide of interest is preferably amplified before or in connection with step a) and most preferably by polymerase chain reaction extension. The invention also comprises a kit for use in analyzing the sequence of a polynucleotide of interest.

10 Claims, 2 Drawing Sheets a)

b)

c)

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:synthetic
      oilgonucleotide

<400> SEQUENCE: 1
gcttccggct cgtatgttgt gtg                                    23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:synthetic
      oilgonucleotide

<400> SEQUENCE: 2
aaagggggat gtgctgcaag gcg                                    23

METHOD OF SEQUENCING

This application is the national phase of PCT/SE96/01464, filed Nov. 13, 1996.

The present invention relates to a method of analyzing the sequence of a polynucleotide of interest. More precisely the invention relates to a method of sequencing both strands of the polynucleotide whereby the strands are immobilized to a solid support.

DNA sequencing is one of the most important technique by which the precise order of nucleotides in a piece of DNA in the genome of living organisms can be determined. There are two well establised methods used: The chemical degradation method by A. Maxam and W. Gilbert and the chain termination method by F. Sanger and A. R. Coulson. Today the sequencing methods are routine processes performed with automated equipment. Most automated sequensers are based on the chain termination method and utilize fluorescent detection.

According to the chain termination method the double stranded polynucleotide to be analyzed is separated in a first step, whereafter a sequencing primer is hybridized to the single strands. The problem with this step is that the re-annealing of the two strands compete with the primer hybridization. A method to avoid this, which has been developed during the last years, is solid phase sequencing. One strand of the double stranded polynucleotide is provided with one member of a specific binding pair. The other member of the binding pair is coated on a solid support. This binding pair is used to bind the polynucleotide to the support. After binding, the polynucleotide is denaturated and the strand without attachment member is washed away, thereby leaving the support with a single strand of polynucleotide attached to it. Then, the sequencing primers are added and there is no competition from re-annealing of the other strand. In this way much more pure sequencing products are obtained. More pure products result in better or sharper bands or signals from the detection instruments. This is very important e.g in detection of mutations. With the solid phase sequencing technique it is also easy to automate the handling of the samples.

Usually, in the solid phase technique only one of the two strands of a double stranded molecule has been provided with a binding member of a specific binding pair. Thereby only one of the two strands have been captured to the solid support and used in the sequencing reaction. It has been believed that only one of the strands can be used, due to the problems related to working with two complementary strands of equal size that tend to re-anneal.

For many applications it is desired to sequence both strands, for example to obtain a double check of the sequencing result. EP 371 437 relates to a solid phase sequencing method which, as one embodiment, utilizes both strands of the molecule. However, in this patent different binding members are attached to the two strands and the strands are captured to two different solid matrices. Thus, also with this method the risk for re-annealing has brought about the need for separate processing of the two strands.

The object of the present invention is to obtain an improved method of sequencing on a solid support.

A further object of the present invention is to present a sequencing method on a solid support by which both strands of a double stranded polynucleotide can be sequenced at the same time on the same solid support.

The objects of the invention are achieved by the method as claimed in the claims. According to the invention a method of analyzing a sequence of a polynucleotide of interest is obtained. The method comprises the steps of:

a) incorporating one member of a specific binding pair at the end of each strand of a double stranded polynucleotide of interest, the member being of the same type for both strands, b) immobilizing both strands of the polynucleotide to a solid support provided with the other member of the specific binding pair, c) annealing sequencing primers to the immobilized strands, d) sequencing both strands by the chain termination method.

It has been found that the solid phase technique makes it possible to capture both strands of a polynucleotide in such an orientation that the tendency of having them re-annealing is avoided or largely reduced. Normally the two strands anneal in a manner that the 5' end of one strand anneal to the 3' end of the complementary strand. It was found that it was possible to attach a binding member to the 5' end of each strand and to capture each strand to the solid support by this binding member. Then the two strands are separated by denaturation or the capture is made under denaturating conditions. The capture of the two strands by their 5' end makes it more difficult for the two strands to "find" each other as the orientation of the strands is "wrong" for annealing to occur. It was surprisingly found that this "wrong" orientation was sufficient to avoid re-annealing. The expected "rearrangement" of the strands to re-anneal did not occur. The method according to the invention makes it possible to sequence both strands of one double stranded DNA at the same time on the same solid support. By using two differently labelled sequencing primers, one for each strand, the double amount of information is obtained from the sequencing reaction. Hence, it is possible to reduce the number of sequencing reactions by half, as two "different" DNA strands can be used as templates in the same sequencing reaction.

Incorporation of one member of the specific binding pair can be accomplished in conventional manners.

According to a prefered embodiment of the invention the polynucleotide of interest is amplified before or in connection with step a) of the method. Different amplification methods can be used such as amplification by a vector, e.g. as described in U.S. Pat. No. 5,405,746. According to this method the member of the specific binding pair is incorporated into the vector DNA by first linearizing the vector with restriction enzymes. Then the binding member is incorporated by ligation or by a DNA polymerase.

In a further prefered embodiment of the invention said polynucleotide is amplified by polymerase chain reaction extension or a first and second amplification primer, one primer being annealed to each strand of the double stranded polynucleotide. Both primers comprise the member of the specific binding pair and the members are of the same type for both primers, i.e. only one type of binding pair is used. In this manner copies of both strands of the polynucleotide bonded to said member of the specific binding pair are produced. The binding member can be incorporated into the 5' end of the primer or internally in the primer.

Polymerase chain reaction (PCR) is a common, well-known amplification method which results in selective amplification of a chosen part of DNA molecule. The part of the DNA molecule is defined by a pair of primers wich are annealed to the molecule, one primer to each strand of the double stranded molecule.

The specific binding pair can be any pair of compounds with strong interaction between the members of the pair. Furter, it must be possible to incorporate one of the members of the pair into deoxynucleotides and to provide a solid support with the other member. The interaction between the members of the pair must be stable through the whole process. Example of such binding pairs are biotin—avidin, biotin—streptavidin, cystein—thiol groups, antigen—antibody, lectin—sugar.

The immobilization of the strands is performed in a conventional manner. The denaturing step can be performed during the immobilization or after. The strands can be separated with well known methods such as temperature increase or NaOH addition.

The solid support used according to the invention can be any one known in the art, e.g. magnetic or other beads, capillaries, microtitre wells. However, preferably the solid support is a manifold having a plurality of individual solid phase members. The solid phase members are adapted for cooperation with a corresponding set of receptacles, which contain the solutions for the different reaction steps. One preferred such system is disclosed in After the immobilization step the conditions are adjusted for sequencing according to any well known standard protocol. The sequencing products are labelled in a suitable manner by introducing known labels. As such can be mentioned an isotope such as $^{32}P$ or a fluorescent group. Preferably the sequencing primers are labelled. They must be differently labelled. Most preferably the labels are two different fluorescent dyes.

The sequencing products are separated and detected by known means, e.g. by gel electrophoresis. If the labels are two different fluorescent dyes, the sequencing products can be detected for example by a two laser instrument. Thereby the products from the sequencing of both strands can be detected simultaneously.

The invention also comprises a kit for use in analyzing the sequence of a polynucleotide of interest. The kit comprises:

(a) a solid support, (b) amplification primers comprising one member of a specific binding pair, the member being of the same type for both primers, (c) sequencing primers.

Preferably the solid support is a manifold having a plurality of individual solid phase members and the sequencing primers are differently labelled with fluorescent dyes.

The method according to the invention can be used for determining one or several nucleotide variations, such as a nucleotide replacement, deletion or insertion, in the polynucleotide of interest. The method is especially suitable for confirmatory sequencing e.g. DNA diagnosis, in forensic analysis, HLA typing.

The invention will now be illustrated with the following example, which however, is not intended to limit the invention.

b) immobilization of biotinylated strands to a solid support; and c) annealing of a blue and red labeled sequencing primer to the strands.

Figure 2:
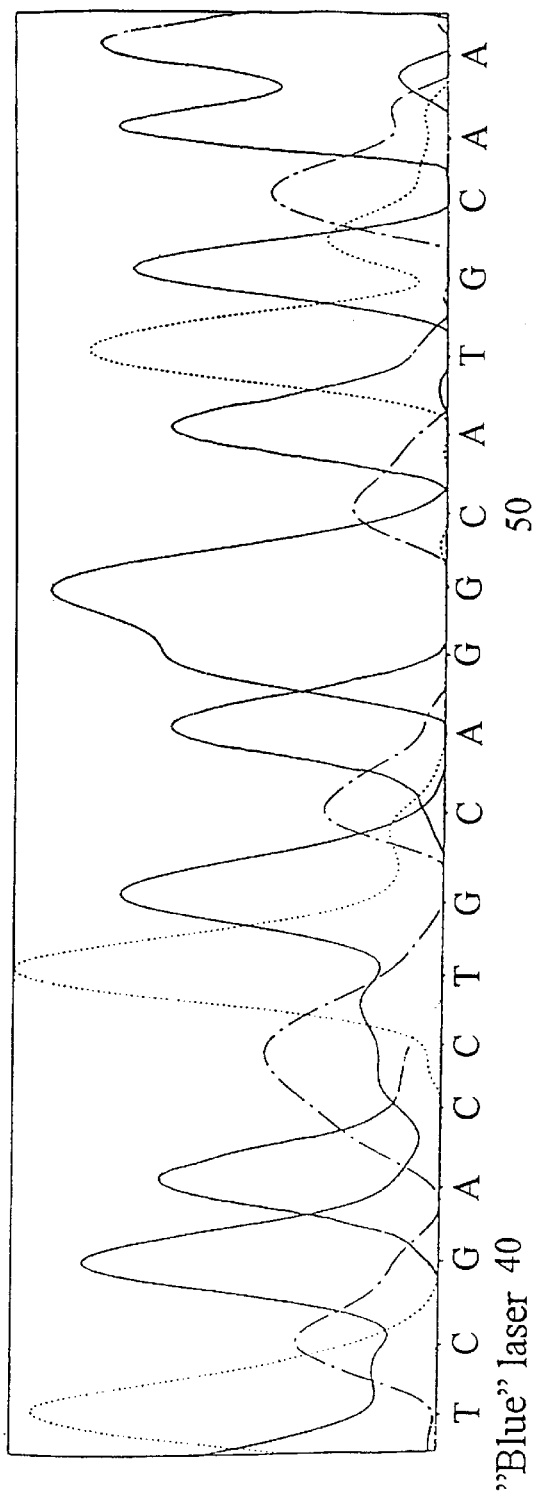
Figure 2:
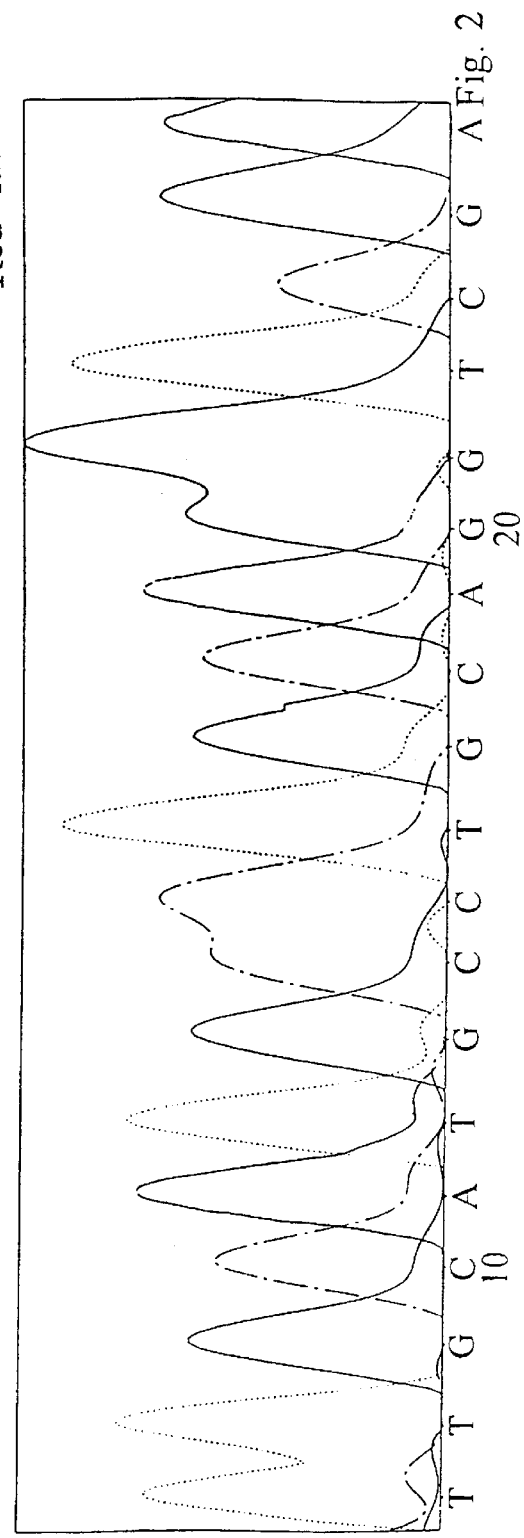

FIG. 2 presents the results obtained with the red label and the blue label in the example.

EXAMPLE

Determination of the sequence of pUC 18 DNA.

Ten different samples of the same sequence were processed at the same time using the AutoLoad™ Solid Phase sequencing kit together with AutoLoad™ Heating Block Inserts from Pharmacia Biotech.

Amplification Reaction

The following components were added to a PCR tube:

5 µl of 10×PCR buffer

5 µl of 10×dNTP solution

2 µl of 5 pmole of each primer

1–2 U (U=units) Taq polymerase from Perkin-Elmer

5–20 ng of pUC 18 template sterile water to obtain a total volume of 50 µl

The tube was processed for 30 cycles where each cycle comprises denaturing at 95° C. for 30 sec. and primer annealing and extension at 70° C. for 120 sec. The amplification was carried out on a GeneAmp™ PCR System 9600 from Perkin-Elmer.

10×PCR buffer: 100 mM Tris-HCl (pH 8.3), 15 mM MgCl$_2$, 500 mM KCl, 1% Tween 20.

10×dNTP: 2 mM of each dNTP Primer: 5'-Biotin-GCT TCC GGC TCG TAT GTT GTG TG-3' (SEQ ID NO 1) 5'-Biotin-AAA GGG GGA TGT GCT GCA AGG CG-3' (SEQ ID NO 2)

Immobilisation of Amplified DNA on Solid Support

As solid support was used a comb with 8 teeth coated with streptavidin. The teeth were arranged on the comb in two rows of 4 teeth. The comb was adapted for use together with well plates. 10 well plates were used in all steps until the sequencing reactions. One row of 4 teeth of the comb was placed in each well. For the sequencing a 40 well plate was used and one tooth of the comb was placed in each well. This is in accordance with FIG. 7 in the above mentioned PCT/SE93/00929

80 µl of a binding/washing solution consisting of 2 M NaCl, 10 mM Tris-HCl (pH 7.5), 1 mM EDTA were added to each well of a 10 well plate. 40–50 µl of the reaction mixture from the PCR reaction were added to each well. The streptavidin coated combs were placed in the wells and were moved up and down gently to obtain mixing. Then the solution was incubated 1 hour at room temperature to ensure complete immobilization of the biotinylated PCR products on the combs.

The immobilized products were washed in the same binding/washing solution as above.

The immobilized DNA was denatured by placing the combs in the wells of a 10 well plate and incubating the combs for 5 minutes. Each well contained 100 µl 0.1 M NaOH solution. The denatured DNA was washed, first with 1×TE buffer (10 mM Tris-HCl, 1 mM EDTA (pH 8)) and then with sterile water.

Sequencing of Immobilized DNA

Primer Annealing

The following components were added to each well of a 10 well plate, whereby one well is required for each PCR product being sequenced:

12 µl annealing buffer (1 M Tris-HCl (pH 7.6), 100 mM MgCl$_2$)

4 pmoles (4 µl) primer 1 (M13 "Universal" primer), labelled with Cy-5™ (red indocarbocyanine fluorophore)

4 pmoles (4 µl) primer 2 (M13 "Reverse" primer), labelled with a "blue" label (fluorescein)

100 µl sterile water

The combs with immobilized DNA were placed in the wells which were heated to 65° C. for 10 minutes. Then the wells were cooled to room temperature for at least ten minutes.

Sequencing Reactions

The following reagents were mixed to four different mixture, the A, C, G and T mixture:

- 30 μl termination mixture of A, C, G or T respectively
- 20 μl annealing buffer
- 10 μl extension buffer
- 120 μl sterile water
- 10 μl diluted T7 DNA polymerase
- 10 μl dimethyl sulphoxide Each termination mixture consists of: 1 mM dATP, 1 mM dCTP, 1 mM dTTP, 1 mM c7dGTP, 50 mM NaCl and 40 mM Tris-HCl (pH 7.6). The A termination mixture further consists of 5 μm ddATP, the C mixture of 5 μm ddCTP, the G mixture of 5 μm of ddGTP and the T mixture of 5 μm of ddTTP.

Annealing buffer used was: 1 M Tris-HCl (pH 7.6) and 100 mM $MgCl_2$.

Extension buffer: 304 mM citric acid, 324 mM DTT (dithiothreitol) and 40 mM $MnCl_2$ (pH 7.5)

T7 DNA polymerase: 8 units/μl in 25 mM Tris-HCl (pH 7.5), 0.25 M NaCl, 5 mM DTT and 50% glycerol. This polymerase solution was diluted with a buffer consisting of Tris-HCl (pH 7.5), 5 mM DTT, 100 μg/ml BSA (bovine serum albumine) and 5% glycerol to a concentration of 2.0 units/μl. 4 μl of this diluted stock solution will be required for each template (set of four reactions).

19 μl of each of A, C, T and G mixture were added to respective well in the 40 well sequencing reaction plate. The plate was heated to 37° C. whereafter the combs were added. The combs were incubated at 37° C. for 5 minutes and then cooled.

The separation and detection of the sequencing products was done on a modified ALF™ DNA Sequencer from Pharmacia Biotech. The sequencer comprises a electrophoresis module for separation and a double laser for detection. Before loading the samples onto the sequencer, 10 μl Stop solution was added to each gel well in the sequencer. The temperature was raised to 50° C. and then the combs were loaded into their respective wells. After 10 minutes of incubation, the combs were removed and the electrophoresis started.

Figure 1:
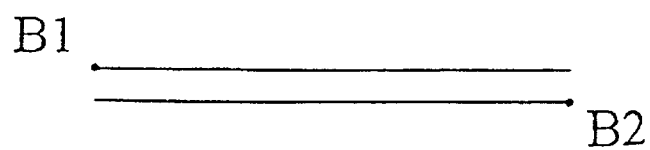
FIG. 1 presents a schematic presentation of the method of this invention, illustrating a) biotin incorporation at the end of each strand of the polynucleotide.
Figure 1:
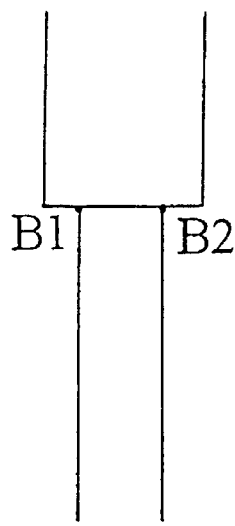
Figure 1:
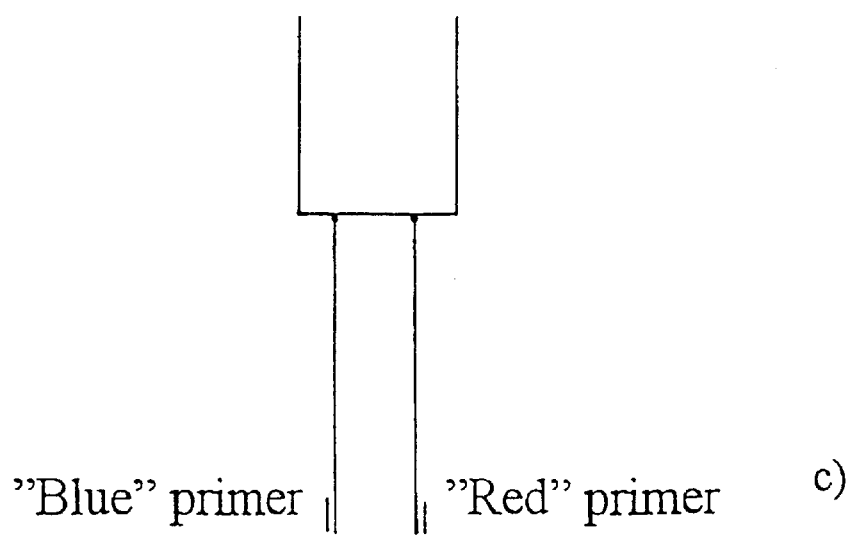

The invention is chematically illustrated in FIG. 1. In FIG 1. a) Biotin (B1 and B2 in FIG. 1) has been incorporated at the end of each strand of a double stranded polynucleotide. In FIG. 1 b) the biotinylated strands have been immobilized to a solid support and in c) a blue and a red sequencing primer respectively, have been annealed to the strands.

The result of the example is shown in FIG. 2. In FIG. 2 the graphs obtained with the red label are shown in the lower plot and the graphs obtained with the blue label in the top plot. If the lower plot is read from the right to the left and the top one from the left to the right, it can be seen that the two plots and thus the two strands complement each other. The first nucleotide of the lower strand is an A which complements the T which is the first nucleotide in the upper strand. The next nucleotide is a G which complements C and C G etc.

---

---

What is claimed is:

1. A method of determining a sequence of a double stranded polynucleotide of interest, comprising the steps of:
   a) incorporating one member of a specific binding pair at the 5' end of each strand of a double stranded polynucleotide of interest, the member being identical for both strands,
   b) immobilizing both strands of the polynucleotide to a solid support provided with the other member of the specific binding pair, wherein said immobilizing results from binding of the members of the specific binding pair to one another,
   c) annealing sequencing primers to the immobilized strands, and
   d) sequencing both strands by the chain termination method.

2. A method according to claim 1, wherein the double stranded polynucleotide of interest is amplified before or during step a).

3. A method according to claim 2, wherein said amplification before or during step a) occurs by polymerase chain reaction extension of a first and second amplification primer, one primer being annealed to each strand of the double stranded polynucleotide, wherein both primers comprise the member of the specific binding pair, the member being identical for both primers, thereby producing copies of both strands of the polynucleotide bonded to said member of the specific binding pair.

4. A method according to claim 1 wherein the immobilization in step b) is made under denaturating conditions.

5. A method according to claim 1 wherein the strands are denatured after immobilization in step b).

6. A method according to claim 1, wherein the sequencing primers are differently labelled.

7. A method according to claim 6, wherein the labels labeling said sequencing primers are different fluorescent dyes.

8. A method according to claim 1, wherein the solid support is a manifold having a plurality of individual solid phase members.

9. A method according to claim 8, wherein the solid phase members are adapted for cooperation with a corresponding set of receptacles.

10. A method according to claim 1, wherein the specific binding pair is selected from biotin—avidin, biotin—streptavidin, cysteine—thiol groups, antigen—antibody, and lectin—sugar.

* * * * *